United States Patent
Colon (10) Patent No.: US 12,070,569 B2
(45) Date of Patent: Aug. 27, 2024

(54) MEDICAL CHECK VALVE FOR FOOD DISTRIBUTION

(71) Applicant: Esteban J Colon, Homestead, FL (US)

(72) Inventor: Esteban J Colon, Homestead, FL (US)

(*) Notice: Subject to any disclaimer, the term of this patent is extended or adjusted under 35 U.S.C. 154(b) by 141 days.

(21) Appl. No.: 17/545,970

(22) Filed: Dec. 8, 2021

(65) Prior Publication Data
US 2023/0173247 A1  Jun. 8, 2023

(51) Int. Cl.
*A61M 39/24* (2006.01)
*A61J 15/00* (2006.01)
*A61M 39/22* (2006.01)

(52) U.S. Cl.
CPC .......... *A61M 39/24* (2013.01); *A61J 15/0015* (2013.01); *A61M 2039/226* (2013.01); *A61M 2039/2433* (2013.01)

(58) Field of Classification Search
CPC .............. A61M 39/223; A61M 39/225; A61M 2039/229
See application file for complete search history.

(56) References Cited

U.S. PATENT DOCUMENTS

| | | | |
|---|---|---|---|
| 4,752,292 A | 6/1988 | Lopez et al. | |
| 5,104,008 A | 4/1992 | Crisci | |
| 7,938,809 B2 | 5/2011 | Lampropouos et al. | |
| 10,668,268 B2 | 6/2020 | Nelson et al. | |
| 2003/0153897 A1 | 8/2003 | Russo | |
| 2017/0281922 A1* | 10/2017 | Baid | A61M 39/22 |
| 2021/0228859 A1* | 7/2021 | Picot | F16K 27/065 |

OTHER PUBLICATIONS

Carmo A/S; Push/pull valve for urine bags and medical bags ; https://www.carmo.dk/en/medical-components/drain-valves/push-pull-valve/ (available as of May 19, 2022).
An Introduction to Your Child's Gastronomy Tube; UC Davis Health, Children's Hospital; p. 3; Rev. Dec. 2019.

* cited by examiner

*Primary Examiner* — Courtney B Fredrickson
(74) *Attorney, Agent, or Firm* — John Rizvi; John Rizvi, P.A.—The Patent Professor®

(57) ABSTRACT

A medical check valve includes a main body with an inlet and an outlet. A poppet valve base in the main body may include a first conduit to enable fluid flow between the inlet and the outlet in a normal operating position and a second conduit to enable fluid flow between the outlet and a top portion of the poppet valve base in a bypass operating position. A poppet cap with a neck portion inserted into the poppet valve base may be moved between an open position and a closed position. In the open position, fluid flow is permitted into an aperture in the cap, e.g., via a syringe, in the bypass operating position such that the fluid in the syringe is delivered to the outlet. In the closed position, and fluid flow is disabled, preventing possible splash back events.

1 Claim, 10 Drawing Sheets

MEDICAL CHECK VALVE FOR FOOD DISTRIBUTION

TECHNICAL FIELD

The present disclosure relates to a medical delivery valve, and more specifically to an enteral tube check valve.

BACKGROUND

Enteral feeding is a medical procedure that may be suitable for a person who has a condition or injury that prevents eating a regular diet by mouth although their gastrointestinal (GI) tract is still able to function. Some of the more common underlying reasons for enteral feeding include: a stroke, which may impair ability to swallow; cancer, which may cause fatigue, nausea, and vomiting that make it difficult to eat; critical illness or injury, which reduces energy or ability to eat; failure to thrive or inability to eat in young children or infants; serious illness, which places the body in a state of stress, making it difficult to take in enough nutrients, and neurological or movement disorders that increase caloric requirements while making it more difficult to eat.

Enteral feeding may include introducing food and nutrients in a liquid medium through a tube that goes directly to the stomach or small intestine. Enteral feeding may make up the person's entire caloric intake or may be used as a supplement.

Some types of enteral feeding methods include nasogastric (NG), which starts in the nose and ends in the stomach, orogastric (OG), which starts in the mouth and ends in the stomach; gastrostomy, which is placed through the skin of the abdomen straight to the stomach, and jejunostomy, which is placed through the skin of the abdomen straight into the intestines.

Healthcare providers may on occasion need to access or change the fluid entering the enteral tube, for example to administer medication. A closed enteral tube check valve may be used to provide access to enteral systems without opening lines, thereby protecting healthcare workers from exposure to potentially infectious bodily fluids or gastric secretions.

SUMMARY

In an embodiment, a medical check valve includes a main body with an inlet and an outlet. A poppet valve base in the main body may include a first conduit to enable fluid flow between the inlet and the outlet in a normal operating position and a second conduit to enable fluid flow between the outlet and a top portion of the poppet valve base in a bypass operating position. The valve may include a handle to rotate the poppet valve base into either of normal or bypass positions, and limiters may be included to provide the user with feedback of whether the valve is in the desired position.

A poppet cap with a neck portion inserted into the poppet valve base may be moved between an open position and a closed position. In the open position, fluid flow is permitted into an aperture in the cap, e.g., via a syringe, in the bypass operating position such that the fluid in the syringe is delivered to the outlet. In the closed position, and fluid flow is disabled, preventing possible splash back events.

DETAILED DESCRIPTION

Figure 1:
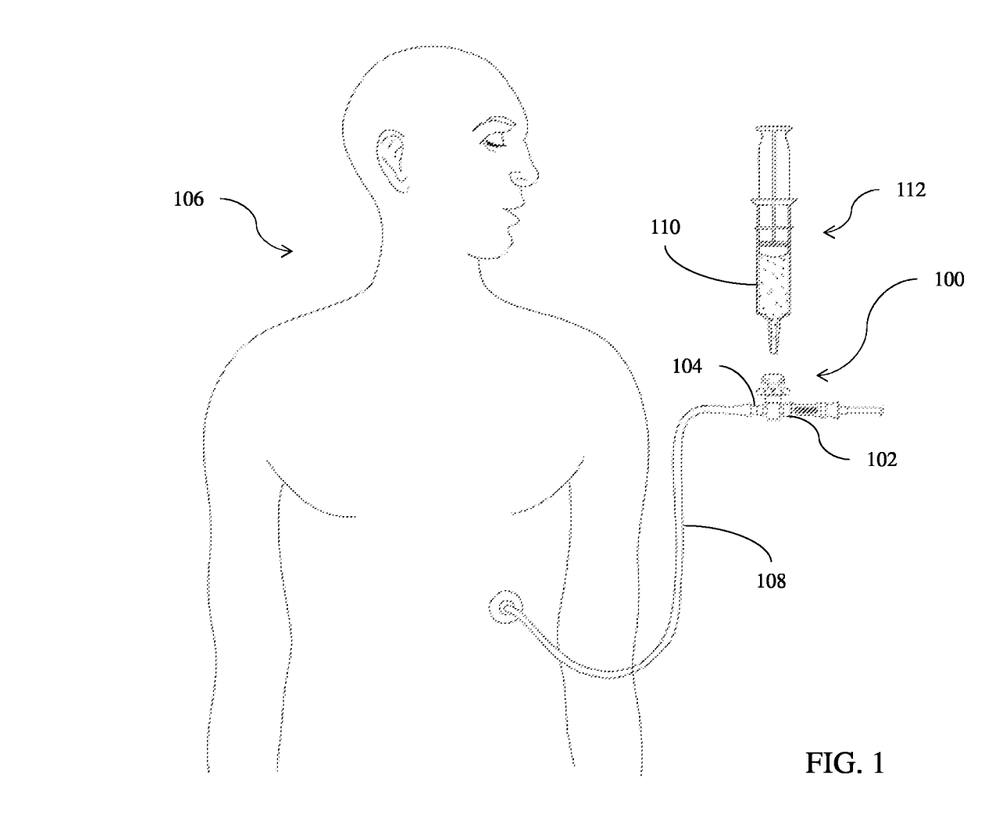
FIG. 1 is a front view of an enteral tube valve system delivering fluid to a patient according to an embodiment.

FIG. 1 shows an enteral valve system 100 according to an embodiment. An inlet connector 102 may connect the valve system to a fluid food/nutrient supply. An outlet connector 104 enables fluid flow from the valve system 100 directly to a patient's 106 gastrointestinal (GI) tract via a surgically implanted tube (enteral tube) 108 according to an embodiment. A healthcare professional may to need to interrupt the flow of fluids from the nutrient supply and administer medicine or other fluids to the patient. In an embodiment, the valve 100 provides a means for introducing such other fluids 110 via a syringe 112.

Figure 2:
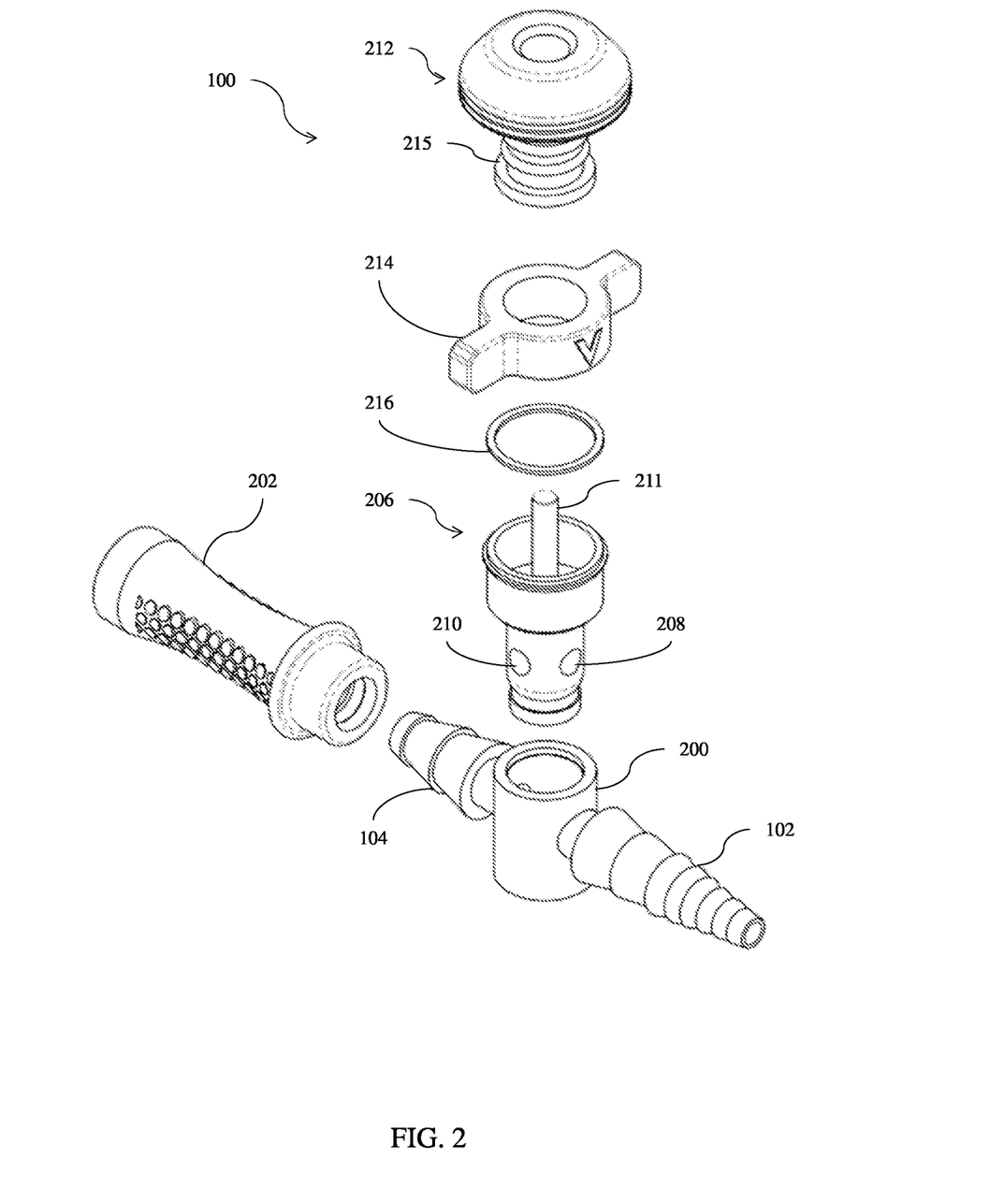
FIG. 2. is an exploded view of the enteral tube valve according to an embodiment.
Figure 3:
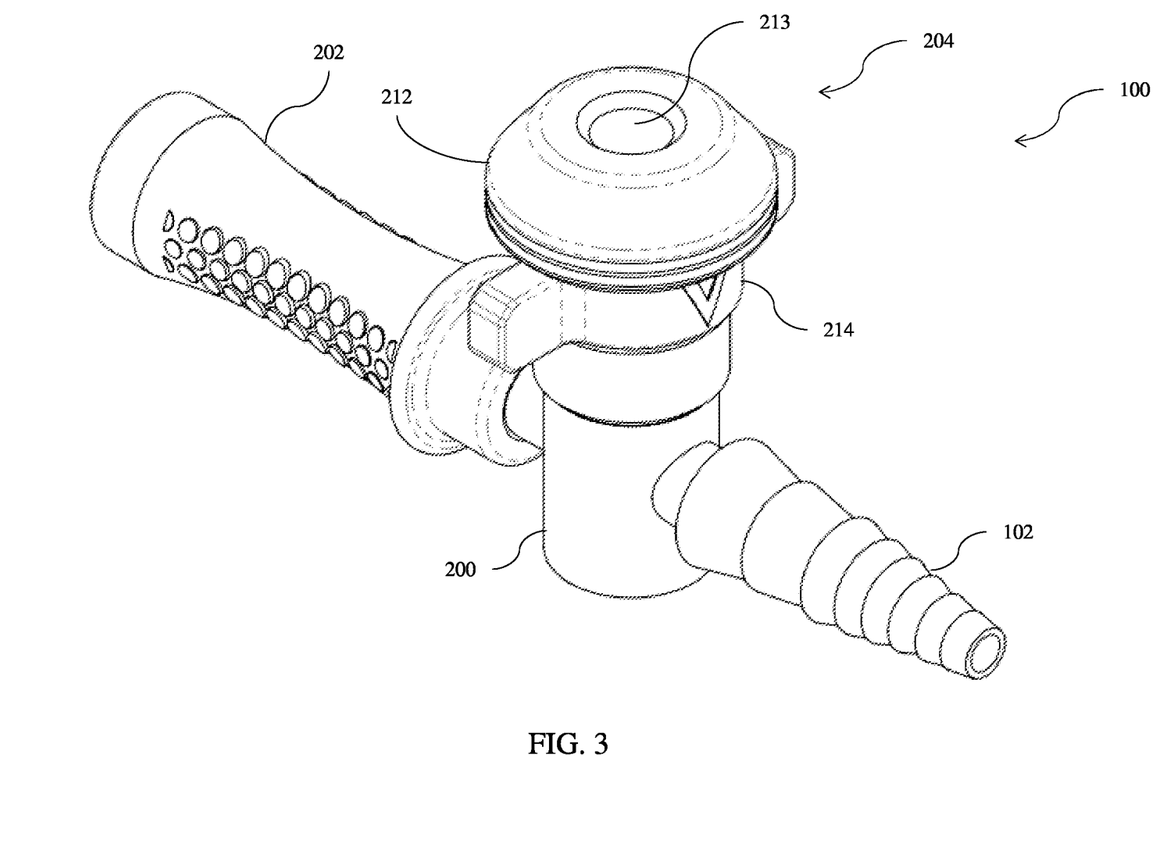
FIG. 3 is a perspective view of the enteral tube valve according to an embodiment.

FIGS. 2 and 3 show an exploded view and assembled view of the valve 100, respectively. The valve includes a main valve body 200 that include the inlet connector 102 and outlet connector 104. A flexible adaptor 202 may be used to pair two male connectors, e.g., the outlet connector 104 and the connector of the enteral tube 108 (see FIG. 1). In an embodiment, the valve body and inlet and outlet connectors may be constructed from a rigid material, such as polycarbonate. However, various materials and production methods may be used to construct the valve system 100. Factors to be considered in selecting the materials and dimensions are rigidity, and ability to be cleaned, sanitized, and avoid clogging.

A poppet valve 204 integral to the valve 100 may be used to accept the syringe 112. A poppet valve base 206 may include a conduit 208 for normal flow from the nutrient supply to the patient via inlet and outlet connectors 102, 104 and conduits 210, 211 to bypass the flow of fluid to the top of the poppet valve for access by the syringe 112. The syringe may be inserted into an aperture 213 in a poppet valve cap 212 to then administer other fluids to the patient.

A handle 214 may be turned to select between normal flow, that is from the feed supply tube (inlet) to the enteral tube (outlet), and bypass flow, that is from the top of the poppet valve to the enteral tube. Stops, e.g., ridges, may be included in the exterior of the poppet valve base 206 and interior of the main valve body 200 to ensure correct positioning of the conduits 208, 210 when the handle is rotated between normal and bypass positions.

The poppet valve cap 212 and handle 214 may be secured to the poppet valve base 206 by a seal 216, e.g., an adhesive or elastomeric O-ring. The poppet valve cap 212 may include a neck portion 215 which may be snapped or press-fit into the interior of the poppet valve base 206. The poppet valve cap and neck portion may be made of a semi-flexible material, such as silicone, rubber, or flexible plastic, to enable a snap fit into the poppet valve base 206.

Figure 4:
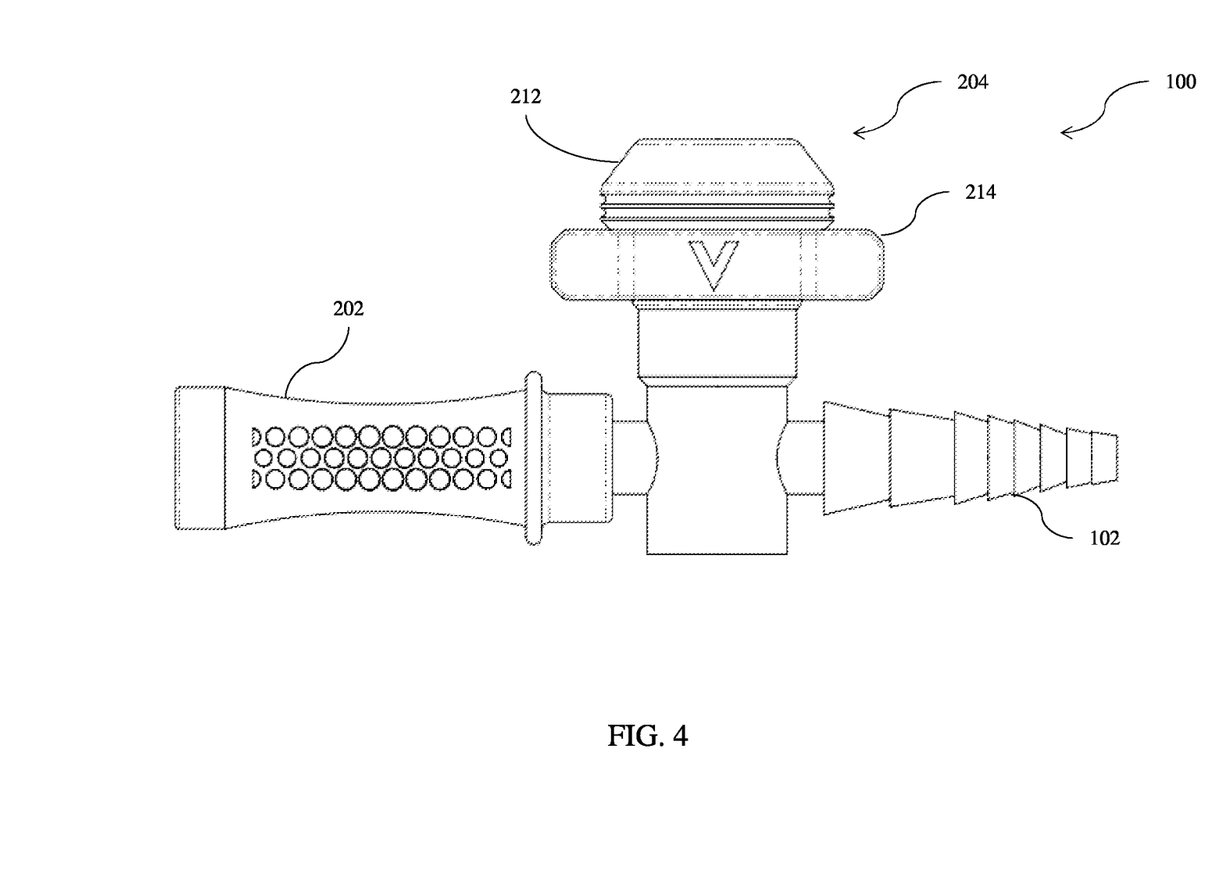
FIG. 4 is a front view of the enteral tube valve in a normal operating position according to an embodiment.
Figure 5:
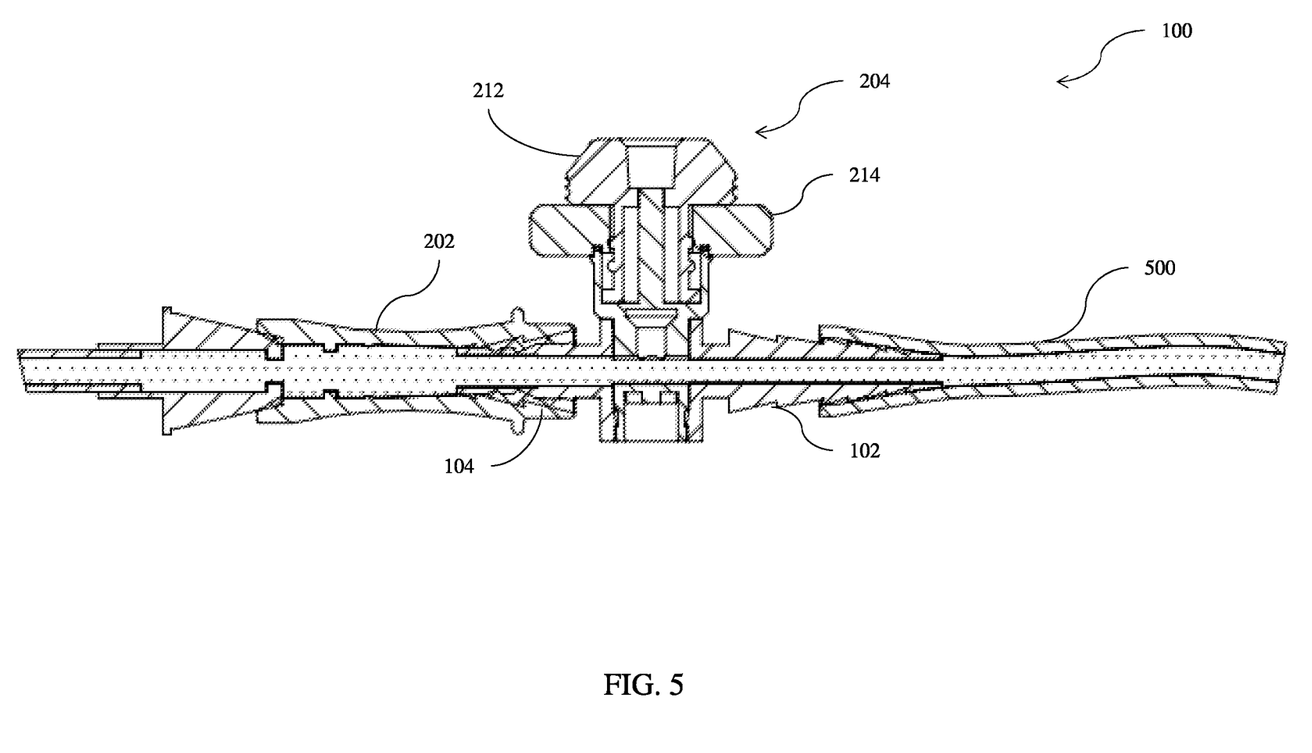
FIG. 5 is a sectional view of the enteral tube valve in a normal operating position according to an embodiment.

FIGS. 4 and 5 show the valve in the normal (open) position and the poppet valve in a "closed" position. The conduit 208 for normal flow passes through the body of the poppet valve base 206, allowing direct fluid flow from the inlet connector 102 to the outlet connector 104. In this embodiment, the male inlet connector 102 is inserted in a feed tube 500, and the male outlet connector 104 is inserted into the flexible adaptor 202 for connection to the male connector of the enteral tube 108.

Figure 6:
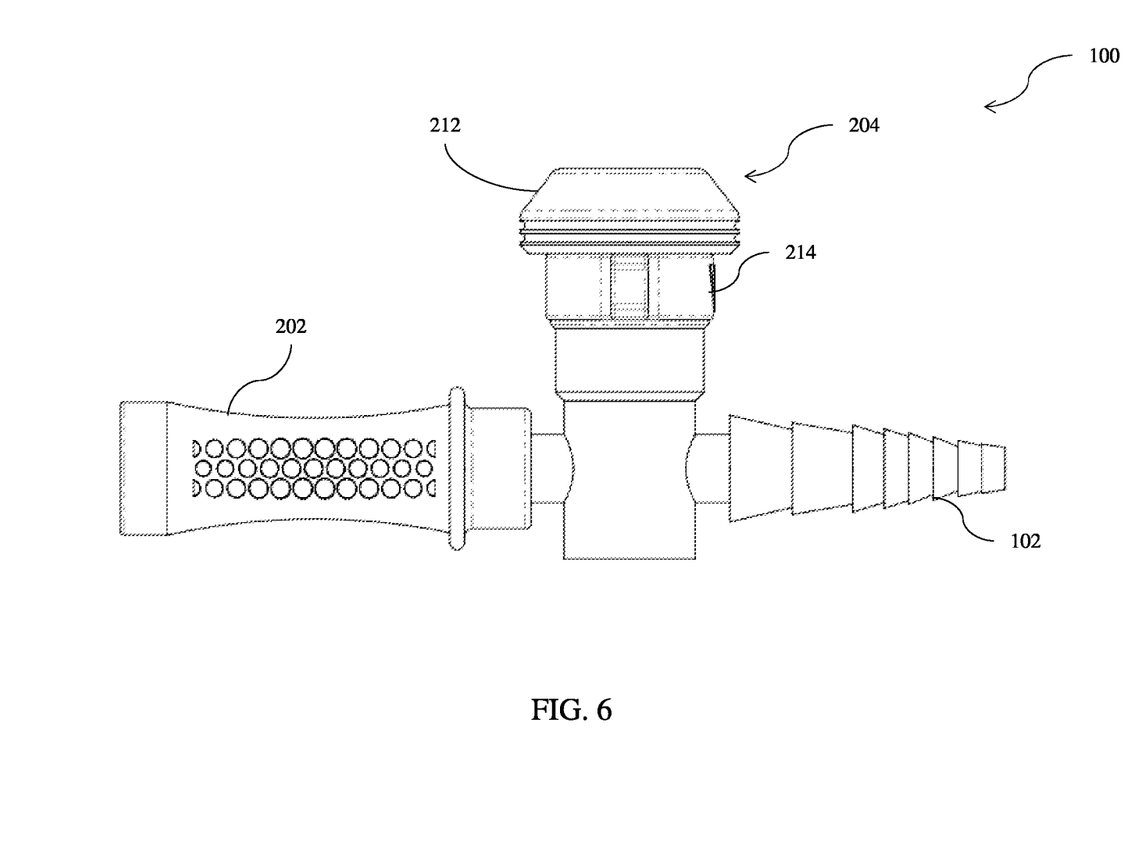
FIG. 6 is a front view of the enteral tube valve in a diverted operating position according to an embodiment.
Figure 7:
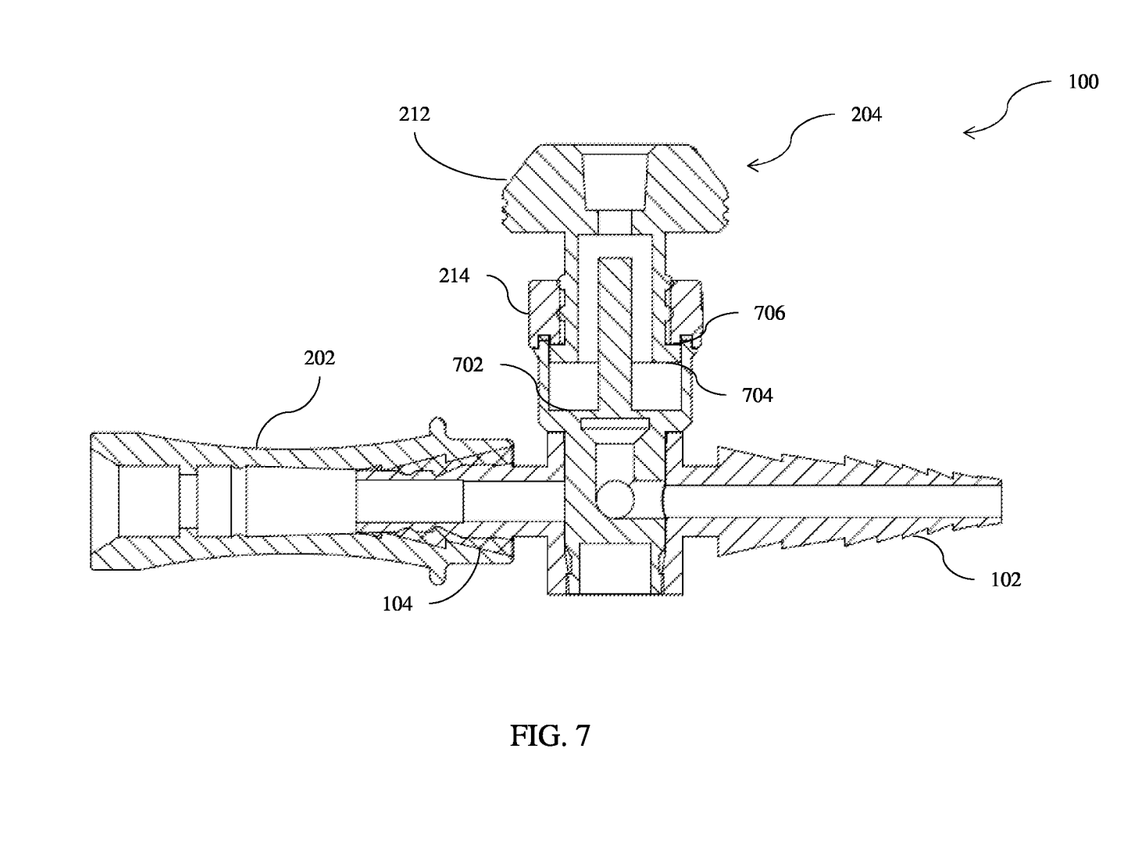
FIG. 7 is a sectional view of the enteral tube valve in a diverted operating position with the poppet valve open according to an embodiment.

FIGS. 6 and 7 show the valve in the bypass position. The handle is rotated such that the conduit 210 aligns with the inlet connector 102. Fluid flow is then bypassed to the poppet valve via conduit 211. FIG. 7 shows the poppet valve in an open position, in which fluid is allowed to pass from the syringe into the enteral feeding tube via the outlet connector 104. The poppet valve base may include an interior surface 702 which meets a lower surface 704 of the poppet cap neck 215 in a fully "closed" position. A ridge 706 of the poppet cap neck 215 may engage with the bottom of the handle in the open position.

Figure 8:
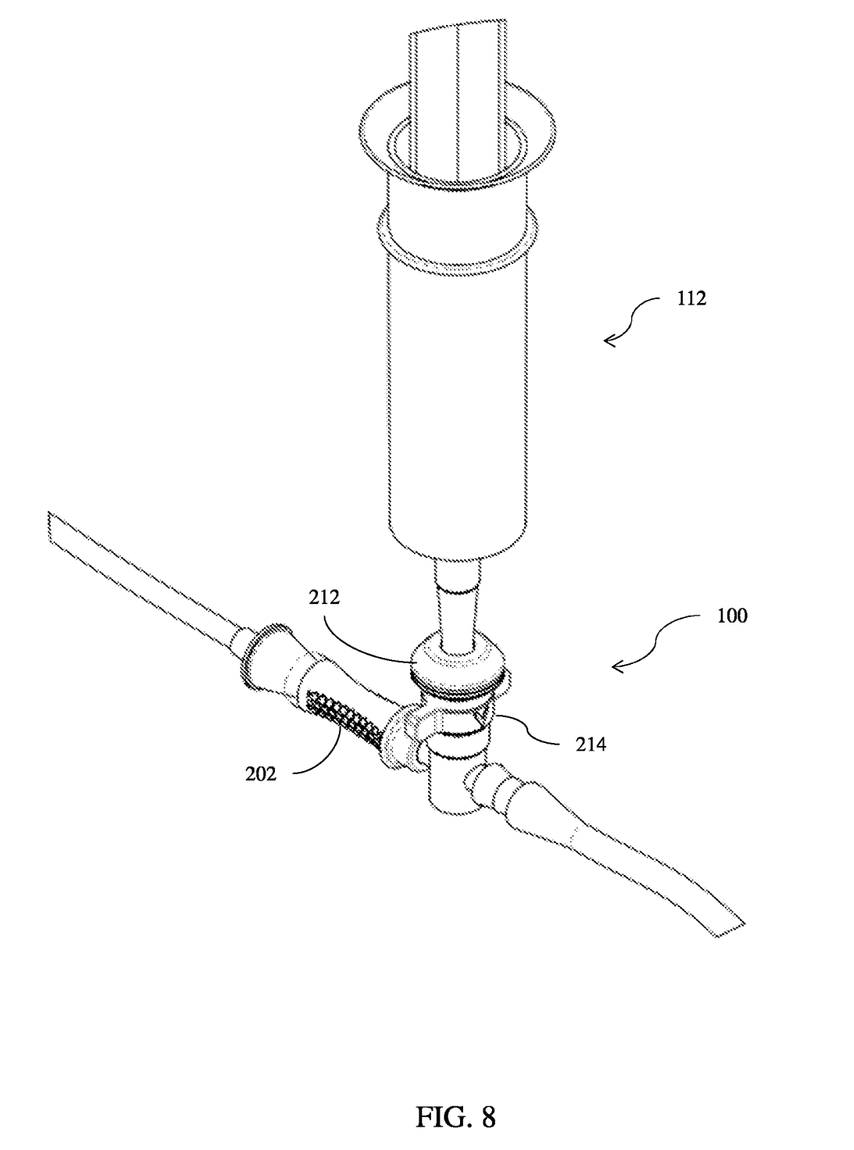
FIG. 8 is a perspective view of the enteral tube valve in a diverted operating position with a syringe inserted in the poppet valve according to an embodiment.
Figure 9:
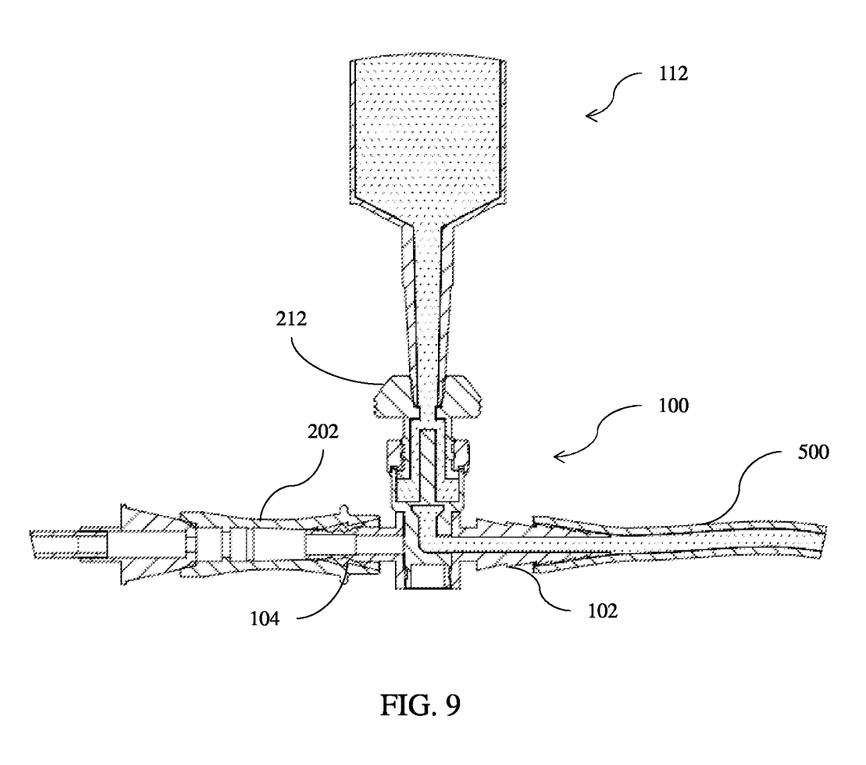
FIG. 9 is a sectional view of the enteral tube valve in a diverted operating position with a syringe inserted in the poppet valve according to an embodiment.
Figure 10:
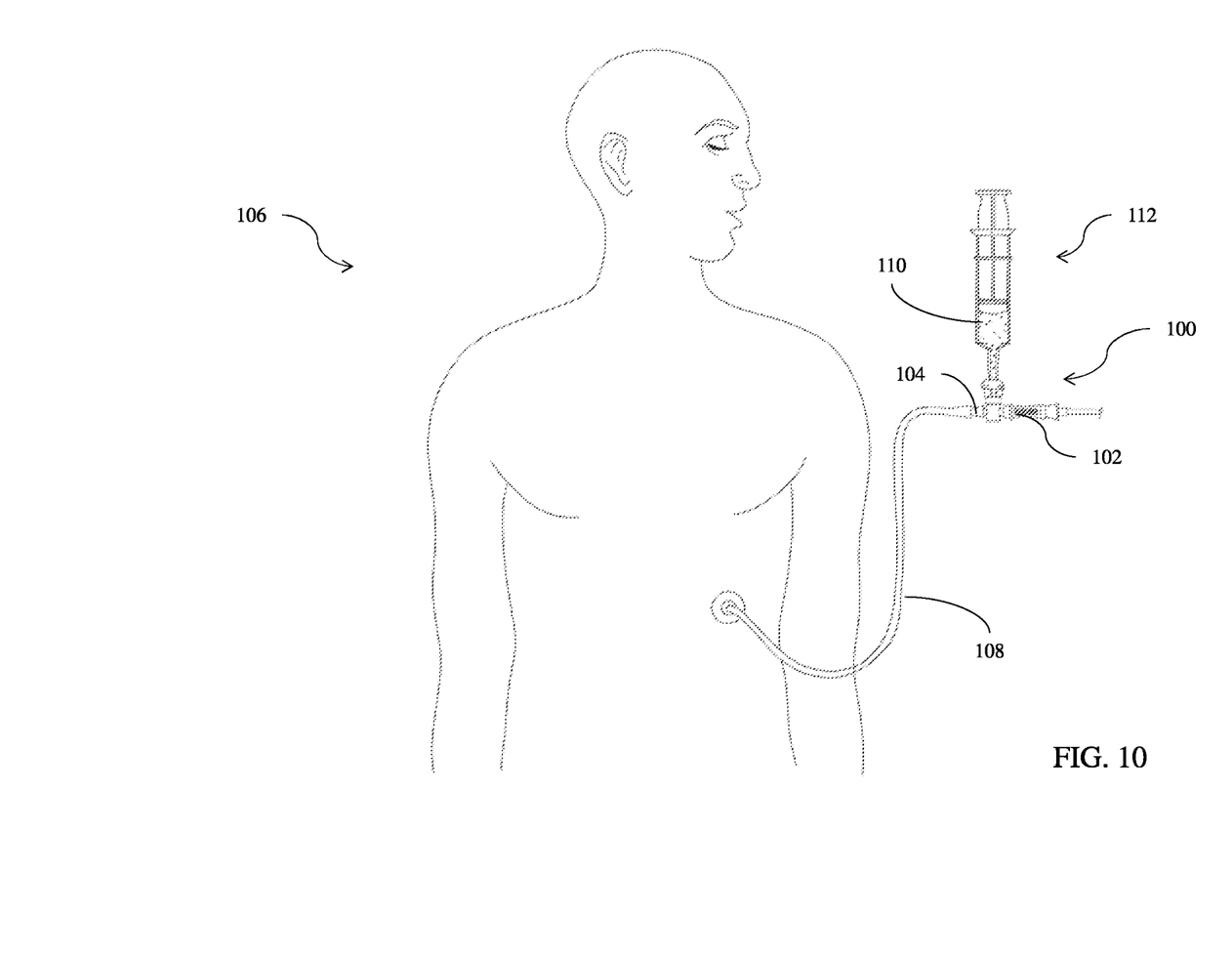
FIG. 10 is a front view of the enteral tube valve system in a diverted operating position delivering fluids to the patient according to an embodiment.

FIGS. 8-10 show an operation of the enteral valve system 100 according to an embodiment. To introduce fluid from the syringe and close off the flow of fluid from the feed tube, the handle is turned from the normal position (FIGS. 4 and 5) to the bypass position (FIGS. 6 and 7). The syringe is then inserted into the aperture of the poppet valve cap 214 (FIG. 8). The poppet valve is then moved into the "open" position by pulling up on the cap (FIG. 9). The contents of the syringe can then flow into the enteral feed tube (FIG. 10).

The preceding description of the disclosed aspects is provided to enable any person skilled in the art to make, implement, or use the claims. Various modifications to these aspects will be readily apparent to those skilled in the art, and the generic principles defined herein may be applied to other aspects without departing from the scope of the claims. For example, in other embodiments, the valve system may also be used with other medical delivery systems, for example, nasogastric (NG) feeding systems. Also, the inlet and outlet connectors may be designed as male-type, female-type, snap, screw-in, etc. types of connectors. Thus, the present disclosure is not intended to be limited to the aspects illustrated herein but is to be accorded the widest scope consistent with the claims disclosed herein.

The invention claimed is:

1. A medical check valve comprising:
 a main valve body having an inlet connector and an outlet connector;
 a poppet valve comprising:
  a poppet valve base rotatable in the main valve body including a first conduit positioned in a body of the poppet valve base to enable a fluid flow from a fluid/nutrient supply to a patient via the inlet connector, and the outlet connector in a normal operating position, and a second conduit positioned in the body of the poppet valve base to enable a fluid flow from a syringe to the patient in a bypass operating position; and
  a poppet valve cap including a neck portion and an aperture, the neck portion comprising a ridge, and is configured to be snapped or press-fit into an interior of the poppet valve base, the aperture is configured to receive the syringe, and the poppet valve cap being mounted in the poppet valve base and movable between an open position enabling fluid flow between the second conduit and the aperture in the bypass operating position, and disabling fluid flow in a closed position; and
 a handle to facilitate rotation of the poppet valve base to place the first conduit and the second conduit in one of the normal operating position and the bypass operating position,
 wherein an exterior of the poppet valve base and an interior of the main valve body include stops to ensure correct positioning of the first conduit and the second conduit when the handle is rotated between the normal operating position and the bypass operating position,
 wherein the poppet valve base includes an interior surface that meets a lower surface of neck portion of the poppet valve cap when the poppet valve cap is in the closed position, and wherein the ridge of the neck portion of the poppet valve cap engages with a bottom of the handle when the poppet valve cap is in the open position.

* * * * *